(12) United States Patent
Drapeau et al.

(10) Patent No.: US 8,586,073 B2
(45) Date of Patent: Nov. 19, 2013

(54) METHODS AND FORMULATIONS FOR ADMINISTRATION OF RESOLVIN ANTI-INFLAMMATORY COMPOUNDS

(75) Inventors: Susan J. Drapeau, Collierville, TN (US); Kelly B. Emerton, Memphis, TN (US); Daniel A. Shimko, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/359,560

(22) Filed: Jan. 27, 2012

(65) Prior Publication Data

US 2013/0195953 A1    Aug. 1, 2013

(51) Int. Cl.
*A61F 2/02* (2006.01)
(52) U.S. Cl.
USPC ........................................... 424/426
(58) Field of Classification Search
None
See application file for complete search history.

(56) References Cited

U.S. PATENT DOCUMENTS

2008/0124400 A1* 5/2008 Liggins et al. ................ 424/501
2008/0280980 A1* 11/2008 Van Dyke ..................... 514/560

OTHER PUBLICATIONS

Xu et al., Resolvins RVE1 and RvD1 attenuate inflammatory pain via central and peripheral cations, 2010, Nature Medicine, vol. 16, pp. 592-597.*

* cited by examiner

*Primary Examiner* — Carlos Azpuru
(74) *Attorney, Agent, or Firm* — Sorell Lenna & Schmidt LLP

(57) ABSTRACT

The invention relates to resolvins and their use as anti-inflammatory compounds. The resolvins may be administered in a variety of forms, including drug depots comprising polymers or lipids. The pharmaceutical formulations of the present invention may be used to treat a variety of conditions including acute pain and chronic pain.

16 Claims, No Drawings

METHODS AND FORMULATIONS FOR ADMINISTRATION OF RESOLVIN ANTI-INFLAMMATORY COMPOUNDS

BACKGROUND

Inflammation in response to infection or tissue damage is usually characterized by heat, redness, swelling and pain at a simple observational level, and be edema, accumulation of leukocytes, and then by accumulation of monocytes and macrophages at a cellular level. Prostaglandins and leukotrienes play a role in the early stages. As tissues return to health, resolvins promote resolution of the leukocytes together with cellular debris, ideally without leaving remnants of host defenses or the invading microorganisms or other inflammatory initiators.

Resolvins are endogenous local mediators with strong anti-inflammatory effects in addition to some immunoregulatory activities at the pico-molar and nano-molar concentrations. They are part of the molecular mechanisms that contribute to the removal of inflammatory cells and restoration of tissue integrity once the need for the inflammatory response is over, i.e., they actively assist in the resolution of inflammation, once believed to be a passive process. It is evident that the presence of aspirin uniquely facilitates this resolution. Thus, at local sites of inflammation, aspirin treatment enhances the conversion of the omega-3 fatty acids EPA and DHA to 18R-oxygenated products, i.e. resolvins of the E and D series, which carry potent anti-inflammatory signals. Two receptors have been identified that mediate the activities of RvE1.

It would be desirable to have modes of administration whereby resolvins could be administered in a safe and effective manner to treat inflammatory conditions.

DETAILED DESCRIPTION OF THE INVENTION

The following description is provided to assist in a comprehensive understanding of exemplary embodiments of the present invention as defined by the claims and their equivalents. It includes various specific details to assist in that understanding, but these are to be regarded as merely exemplary. Accordingly, those of ordinary skill in the art will recognize that various changes and modifications of the embodiments described herein can be made without departing from the scope and spirit of the invention. In addition, descriptions of well-known functions and constructions may be omitted for clarity and conciseness.

The terms and words used in the following description and claims are not limited to the bibliographical meanings, but, are merely used by the inventor to enable a clear and consistent understanding of the invention. Accordingly, it should be apparent to those skilled in the art that the following description of exemplary embodiments of the present invention is provided for illustration purpose only and not for the purpose of limiting the invention as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

The present invention relates to new systems and strategies for treatment of conditions related to inflammation. In particular, the present invention relates to methods and formulation for administering a class of compounds known as resolvins in a suitable carrier.

Resolvins used in the methods and compositions of the present invention may be prepared in vivo or in vitro and then substantially purified and isolated by techniques known in the art (see, for example, U.S. Pat. No. 6,670,396 which is incorporated by reference in its entirety.) Without limitation, the purity of the compounds is generally at least 90%, preferably at least 95%, and most preferably at least about 99%. Certain resolvins used in the present invention may be prepared by chemically modifying one or more of the purified compounds. For example, a purified compound may be chemically modified into a pharmaceutically acceptable salt or prodrug. Additionally or alternatively, one or more hydroxyl, thiol or amino groups of the molecule may be protected using methods well known in the art. Resolvins can also be manufactured independently using conventional methods.

In the present invention, resolvins are delivered via a suitable carrier to treat an inflammatory condition. Examples of inflammatory conditions or diseases that could be treated using resolvin therapy include, but are not limited to, rheumatoid arthritis (RA), dermatitis, multiple sclerosis, ankylosing spondylitis and osteoarthritis. Further, vascular inflammatory disease could be treated, including but not limited to, vasculitis, rheumatoid vaculitis, Buerger's Disease, and cryoglobulinemia. In addition, resolvins have activity as neuroprotectants and may be used for this purpose according to the methods of the present invention.

The resolvins of the present invention may also be used to treat conditions associated with acute or chronic inflammation. Chronic inflammation is associated with a number of conditions and diseases, including but not limited to, disc herniation, facet joint disorders, and periodontal disease.

The term "periodontal disease" as used herein includes all diseases of the periodontal tissue that surround and support the teeth (see, for example, D. M Williams et al., "Pathology of Periodontal Disease", 1992 Oxford University Press). These include gingival, cementum, periodontal ligament, alveolar process bone, and dental supporting bone. Periodontal diseases include, but are not limited to gingivitis and periodontitis.

A "therapeutically effective amount" or "effective amount" is such that when administered, the drug results in alteration of the biological activity, such as, for example, inhibition of inflammation, improvement of the condition, etc. It will be understood that the dosage administered to a patient can be as a single dose, or multiple doses, continuous doses (e.g. continuous infusion) or depot or multiple depots depending on a variety of factors, including the drug's administered pharmacokinetic properties, the route of administration, patient conditions and characteristics, extent of symptoms, concurrent treatment, frequency of treatment and the effect desired.

Administration of resolvins or compositions of the present invention will be in a dosage such that the amount delivered is effective for the intended purpose. The best route of administration, formulation and dosage administered will be dependent on the nature, size and location of the particular site to be treated, the age, presence of any infection, weight and health condition of the patient as well as upon the potency, bioavailability and in vivo half-life of the composition used. Using the teachings of the present specification, the attending physician can readily determine these factors. Alternatively or additionally, the dosage to be administered can be determined from studies using animal models for the particular type of site or disease to be treated. The total dose required for each treatment may be administered by multiple doses or in a single dose. Adjusting the dose to achieve maximal efficacy based on these or other methods are well known in the art and are within the capabilities of trained physicians.

It is critical that the resolvin therapy be administered in a therapeutically effective manner. Oral administration of resolvins is generally not effective. The present invention relates to therapeutically effective modes of administration. In the present invention, resolvins are administered to a subject using a pharmaceutically acceptable carrier to treat conditions associated with inflammation. It is particularly important that a suitable carrier be chosen to treat the condition. The carrier can be employed to achieve various results and functions. For example, the carrier may aid in the delivery kinetics of the treatment and prevent a single bolus of the resolvin therapy, or be used to prevent having to administer repeatedly. The carrier could also function to maintain space in the implanted area.

In various embodiments of the present invention, the resolvin is contained in a drug depot. A drug depot comprises a physical structure to facilitate implantation and retention in a desired site (e.g. a synovial joint, a disc space, a spinal canal, abdominal area, a tissue of the patient, etc.) The drug depot also comprises the drug. The term "drug" as used herein is generally meant to refer to any substance that alters the physiology of the patient. The term "drug" may be used interchangeably herein with the terms "therapeutic agent", "therapeutically effective amount", and "active pharmaceutical ingredient" or "API". It will be understood that a "drug" formulation may include more than one therapeutic agent for delivery to the site. In various embodiments, the drug depot provides an optimal drug concentration gradient of the therapeutic agent at a distance of up to about 0.1 cm to about 5 cm from the implant site.

A "depot" includes but is not limited to capsules, microspheres, microparticles, microcapsules, microfibers particles, nanospheres, coating, matrices, wafters, pills, pellets, emulsions, liposomes, micelles, gels or other pharmaceutical delivery compositions. Suitable materials for the depot are ideally pharmaceutically acceptable biodegradable materials that are preferably FDA approved or GRAS materials. These materials can be polymeric or non-polymeric, as well as synthetic or naturally occurring, or a combination thereof. The depot may also comprise a drug pump.

The term "biodegradable" includes that all or parts of the drug depot will degrade over time by the action of enzymes, by hydrolytic action and/or by other similar mechanisms in the human body. In various embodiments, "biodegradable" includes that the depot (e.g. microparticle, microsphere, gel, etc.) can break down or degrade within the body to non-toxic components after or while a therapeutic agent has been or is being released. By "bioerodible" it is meant that the depot and/or gel will erode or degrade over time due, at least in part, to contact with substances founds in the surrounding tissue, fluids or by cellular action. By "bioabsorbable" it is meant that the depot will be broken down and absorbed within the human body, for example, by a cell or tissue. "Biocompatible" means that the depot will not cause substantial tissue irritation or necrosis at the target tissue site.

In various embodiments, the depot may comprise a biocompatible, bioabsorbable, and/or biodegradable biopolymer that may provide immediate release, sustained release or controlled release of the drug. Examples of suitable sustained release biopolymers include but are not limited to poly (alpha-hydroxy acids), poly (lactide-co-glycolide) (PLGA), polylactide (PLA), polyglycolide (PG), polyethylene glycol (PEG), PEG 200, PEG 300, PEG 400, PEG500, PEG 550, PEG 600, PEG 700, PEG 800, PEG 900, PEG 1000, PEG 1450, PEG 3350, PEG 4500, PEG 8000, conjugates of poly (alpha-hydroxy acids), polyorthoesters, polyaspirins, polyphospagenes, collagen, starch, pre-gelatinized starch, hyaluronic acid, chitosans, alginates, albumin, fibrin, vitamin E analogs, such as alpha tocopheryl acetate, d-alpha tocopherol succinate, D,L-lactide, or L-lactide, caprolactone, dextrans, vinylpyrrolidone, polyvinyla alcohol (PVA), PVA-g-PLGA, PEGT-PBT copolymer (polyactive), metacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate), hydroxypropyl cellulose, hydroxypropyl methylcellulose, carboxymethyl cellulose or salts thereof, Carbopol, poly (hyxroxyehtylmethacrylate), poly (methoxyethylmethacrylate), poly (methoxyethoxyethylmethacyrlate, polymethylmethacyrylate, methylmethacrylate (MMA), gelatin, polyvinyl acholos, propylene glycol or combinations thereof.

In various embodiments, when the drug depot comprises a polymer, it is employed at about 10 wt % to about 99 wt % or about 30 wt % to about 60 wt % based on the weight of the drug depot. In various embodiments, the drug depot comprises PLGA, PLA, PGA, D-lactide, D,L-lactide, L-lactide, D,L-lactide-ϵ-caprolactone, gycolide-caprolactone or a combination thereof.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers, drug release adjusting agents; emulsifiers; preservatives such as benzalkonium chloride, chlorobutanol, phenylmercuric acetate and phenylmercuric nitrate, sodium bisulfite, sodium bisulfate, sodium thiosulfate, thimerosal, methylparaben, polyvinyl alcohol and phenylethyl alcohol, solubility adjusting agents; stabilizers; and/ or cohesion modifiers. Typically, any such inactive materials will be present within the range of 0-75 wt. % and more typically within the range of 0-30 wt. %. If the depot is to be placed in the spinal area or joint area, in various embodiments, the depot may comprise sterile preservative free material.

The depot can be different sizes, shapes and configurations. There are several factors that can be taken into consideration in determining the size, shape and configuration of the drug depot. For example, both the size and shape may allow for ease of positioning the drug depot at the target tissue site that is selected as the implantation or injection site. In addition, the shape and size of the system should be selected so as to minimize or prevent the drug depot from moving after implantation or injection. In various embodiments, the drug depot can be shaped like a sphere, a cylinder such as a rod or fiber, a flat surface such as a disc, film, ribbon or sheet, or the like. Flexibility may be a consideration so as to facilitate placement of the drug depot. In various embodiments, the drug depot can be different sizes, for example, the drug depot may be a length of form about 0.01 mm to 5 mm and have a diameter form about 0.01 to 2 mm. In various embodiments, the drug depot may have a layer thickness of form about 0.005 to 1.0 mm, such as, for example, from 0.05 to 0.75 mm.

Radiographic markers may be included on the drug depot to permit the user to accurately position the depot into the target site of the patient. These radiographic markers will also permit the user to track movement and degradation of the depot at the site over time. In this embodiment, the user may accurately position the depot in the site using any of the numerous diagnostic imaging procedures. Such diagnostic procedures include, for example, X-ray imaging or fluoroscopy. Examples of such radiographic markers include, but are not limited to, barium, calcium, and/or metal beads or particles. When present, the radiographic marker is typically present in an amount of from about 10% to about 40% as well as ranges between any two of these values, e.g. 10-15%, 15-20%, 20-25%, 25-30%, 30-35%, 35-40% and so forth. In various embodiments, the radiographic marker can be a spherical shape or ring around the depot.

In one embodiment, a drug depot for delivering a therapeutic agent to a target tissue site beneath the skin of a patient is provided, the drug depot comprising an effective amount of a resolvin, wherein the target tissue site comprises at least one muscle, ligament, tendon, cartilage, spinal disc, spinal foraminal space near the spinal root, facet or synovial joint or spinal canal.

In embodiments where the drug depot is a gel, in contrast to a sprayable gel that typically employs a low viscosity polymer, a gel with a higher viscosity may be desirable for other applications, for example a gel having a putty-like consistency may be more preferable for the indications as set forth in the instant application.

In another embodiment, a viscous gel is provided that is loaded with one or more drug depots (e.g. microspheres loaded with a therapeutic agent), wherein the viscous gel is positioned into a synovial joint, disc space, a spinal canal, or a soft tissue surrounding the spinal canal of a subject. The gel can also be used, in various embodiments, to seal or repair tissue. In yet another embodiment, the gel is injectable, and/or an adherent gel that solidifies with contact with tissue. For example, the gel may be administered as a liquid that gels in situ at the target tissue site. In various embodiments, the gel can comprise a two part system where a liquid is administered and a gelling agent is added subsequently to cause the liquid or gel to harden.

In various embodiments, the drug depot is loaded with a resolvin and optionally one or more therapeutic agents and delivered to the desired target tissue site, and in various embodiments, the drug depot may be held in place by a suture, barb, staple, adhesive gel, etc. which prevents the drug depot from being removed from that site by the venous systemic circulation or otherwise dispersed too widely, which reduces the desired therapeutic effect. For example, after hours or days, the drug depot may degrade, thereby allowing the drug depots (e.g., microspheres) to begin releasing the therapeutic agent. The microspheres do not begin releasing the agent until they are released from the drug depot. So, the microspheres may be formed from an insoluble or inert substances, but soluble or active once it comes into contact with the target tissue site. Likewise, the drug depot may comprise a substance that dissolves or disperses within the tissue. As the drug depot begins to dissolve within hours to days, the drug depots (e.g., microspheres) are exposed to body fluids and begin releasing their contents. The drug depot can be formulated to optimize exposure time of the drug depot and release of the therapeutic agent from the drug depot. In various embodiments, the drug depot (e.g., gel) is flowable and can be injected, sprayed, instilled, and/or dispensed to, on or in the target tissue site. "Flowable" means that the gel formulation is easy to manipulate and may be brushed, sprayed, dripped, injected, shaped and/or molded at or near the target tissue site as it coagulates. "Flowable" includes formulations with a low viscosity or water-like consistency to those with a high viscosity, such as a paste-like material. In various embodiments, the flowability of the formulation allows it to conform to irregularities, crevices, cracks, and/or voids in the tissue site. For example, in various embodiments, the gel may be used to fill one or more voids in an osteolytic lesion.

In various embodiments, the drug depot comprises poly (alpha-hydroxy acids), poly (lactide-co-glycolide) (PLGA), polylactide (PLA), polyglycolide (PG), polyethylene glycol (PEG) conjugates of poly (alpha-hydroxy acids), polyorthoesters, polyaspirins, polyphosphagenes, collagen, starch, pregelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG (poly(d,l-lactide-co-glycolide), PLA-PLGA, poloxamer 407, PEG-PLGA-PEG triblock copolymers, SAIB (sucrose acetate isobutyrate) or combinations thereof. These one or more components allow the therapeutic agent to be released from the drug depot in a controlled and/or sustained manner. For example, the drug depot containing the therapeutic agent and a polymer matrix can be injected at the target tissue site and the polymer matrix breaks down over time (e.g., hours, days) within the target tissue site releasing a resolvin and optionally additional therapeutic agents. Thus the administration of the drug depot can be localized and occur over a period of time (e.g., at least one day to about 2, 3, 4, 5, 6, 7, 8, 9, 10 days or months). In some embodiments, the therapeutically effective dosage amount (e.g., resolvin) and the release rate profile are sufficient to reduce inflammation and/or pain for a period of at least one day, for example, 1-90 days, 1-10 days, 1-3 days, 3-7 days, 3-12 days; 3-14 days, 7-10 days, 7-14 days, 7-21 days, 7-30 days, 7-50 days, 7-90 days, 7-140 days, 14-140 days, 3 days to 150 days, or 3 days to 6 months or 1 year.

The terms "sustained release" (e.g., extended release or controlled release) are used herein to refer to one or more therapeutic agent(s) that is introduced into the body of a human or other mammal and continuously releases a stream of one or more therapeutic agents over a predetermined time period and at a therapeutic level sufficient to achieve a desired therapeutic effect throughout the predetermined time period. Reference to a continuous release stream is intended to encompass release that occurs as the result of biodegradation in vivo of the drug depot, or a matrix or component thereof, or as the result of metabolic transformation or dissolution of the therapeutic agent(s) or conjugates of therapeutic agent(s).

In various embodiments, the drug depot can be designed to cause an initial burst dose of therapeutic agent within the first 24 hours after implantation. "Initial burst" or "burst effect" or "bolus dose" refers to the release of therapeutic agent from the drug depot during the first 24 hours after the drug depot comes in contact with an aqueous fluid (e.g., synovial fluid, cerebral spinal fluid, etc.). In various embodiments, the drug depot is designed to avoid this initial burst effect.

In various embodiments, the drug depot contains one or more different release layer(s) that releases a bolus dose of a resolvin or pharmaceutically acceptable salt thereof (e.g., 5 mg to 60 mg at a target site beneath the skin) and one or more sustain release layer(s) that releases an effective amount of a resolvin or pharmaceutically acceptable salt thereof over a period of one day to 6 months. In various embodiments, the one or more immediate release layer(s) comprise PLGA, which degrades faster and than the one or more sustain release layer(s), which comprises PLA, which degrades at a slower rate than the PLGA.

In various embodiments, when the drug depot comprises a gel, the gel may have a pre-dosed viscosity in the range of about 1 to about 500 centipoise (cps), 1 to about 200 cps, or 1 to about 100 cps. After the gel is administered to the target site, the viscosity of the gel will increase and the gel will have a modulus of elasticity (Young's modulus) in the range of about $1 \times 10^4$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

In one embodiment, the gel may be an adherent gel, which comprises a therapeutic agent that is evenly distributed throughout the gel. The gel may be of any suitable type, as previously indicated, and should be sufficiently viscous so as to prevent the gel from migrating from the targeted delivery site once deployed; the gel should, in effect, "stick" or adhere to the targeted tissue site. The gel may, for example, solidify upon contact with the targeted tissue or after deployment from a targeted delivery system. The targeted delivery system may be, for example, a syringe, a catheter, needle or cannula or any other suitable device. The targeted delivery system may inject or spray the gel into or on the targeted tissue site. The therapeutic agent may be mixed into the gel prior to the gel being deployed at the targeted tissue site. In various embodiments, the gel may be part of a two-component delivery system and when the two components are mixed, a chemical process is activated to form the gel and cause it to stick or adhere to the target tissue.

In various embodiments, for those gel formulations that contain a polymer, the polymer concentration may affect the rate at which the gel hardens (e.g., a gel with a higher concentration of polymer may coagulate more quickly than gels having a lower concentration of polymer). In various embodiments, when the gel hardens, the resulting matrix is solid but is also able to conform to the irregular surface of the tissue (e.g., recesses and/or projections in bone).

The percentage of polymer present in the gel may also affect the viscosity of the polymeric composition. For example, a composition having a higher percentage by weight of polymer is typically thicker and more viscous than a composition having a lower percentage by weight of polymer. A more viscous composition tends to flow more slowly. Therefore, a composition having a lower viscosity may be preferred in some instances, for example when applying the formulation via spray.

In various embodiments, the molecular weight of the gel can be varied by many methods known in the art. The choice of method to vary molecular weight is typically determined by the composition of the gel (e.g., polymer, versus non-polymer). For example in various embodiments, when the gel comprises one or more polymers, the degree of polymerization can be controlled by varying the amount of polymer initiators (e.g. benzoyl peroxide), organic solvents or activator (e.g. DMPT), crosslinking agents, polymerization agent, and/or reaction time.

Suitable gel polymers may be soluble in an organic solvent. The solubility of a polymer in a solvent varies depending on the crystallinity, hydrophobicity, hydrogen-bonding and molecular weight of the polymer. Lower molecular weight polymers will normally dissolve more readily in an organic solvent than high-molecular weight polymers. A polymeric gel, which includes a high molecular weight polymer, tends to coagulate or solidify more quickly than a polymeric composition, which includes a low-molecular weight polymer. Polymeric gel formulations, which include high molecular weight polymers, also tend to have a higher solution viscosity than a polymeric gel, which include a low-molecular weight polymer.

In various embodiments, the gel can have a viscosity of about 300 to about 5,000 centipoise (cp). In other embodiments, the gel can have a viscosity of from about 5 to about 300 cps, from about 10 cps to about 50 cps, from about 15 cps to about 75 cps at room temperature, which allows it to be sprayed at or near the target site.

In various embodiments, the drug depot may comprise material to enhance viscosity and control the release of the drug such material may include, for example, hydroxypropyl cellulose, hydroxypropyl methylcellulose, hydroxyethyl methylcellulose, carboxymethylcellulose and salts thereof, Carbopol, poly(hydroxyethylmethacrylate), poly(methoxyethylmethacrylate), poly(methoxyethoxy-ethylmethacrylate), polymethyl-methacrylate (PMMA), methylmethacrylate (MMA), gelatin, polyvinyl alcohols, propylene glycol, PEG 200, PEG 300, PEG 400, PEG 500, PEG 550, PEG 600, PEG 700, PEG 800, PEG 900, PEG 1000, PEG 1450, PEG 3350, PEG 4500, PEG 8000 or combinations thereof. For example, in various embodiments, the drug depot comprises from about 2.5% to 60% by weight of a resolvin, which is sprayed with from about 40% to 60% by weight PLGA, 5% to 40% by weight of PEG550.

In various embodiments, the molecular weight of the polymer can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to 50,000.

When there are other active ingredients, surfactants, excipients or other ingredients or combinations thereof in the formulation, in some embodiments, these other compounds or combinations thereof comprise less than 20 wt. %, less than 19 wt. %, less than 18 wt. %, less than 17 wt. %, less than 16 wt. %, less than 15 wt. %, less than 14 wt. %, less than 13 wt. %, less than 12 wt. %, less than 11 wt. %, less than 10 wt. %, less than 9 wt. %, less than 8 wt. %, less than 7 wt. %, less than 6 wt. %, less than 5 wt. %, less than 4 wt. %, less than 3 wt. %, less than 2 wt. %, less than 1 wt. % or less than 0.5 wt. %. Exemplary excipients include but are not limited to mPEG, D-Sorbital, maltodextran, cyclodextrin and combinations thereof.

The drug depot release profile can also be controlled, among other things, by controlling the particle size distribution of the components of the drug depot. In various embodiments, the particle size distribution of the components of the drug depot (e.g., resolvin, gel, etc.) may be in the range of from about 10 μM to 100 μM so that the drug depot can easily be delivered to or at or near the target site by injection, spraying, instilling, etc.

In some embodiments, at least 75% of the particles have a size from about 1 micrometer to about 250 micrometers. In some embodiments, at least 85% of the particles have a size from about 5 micrometer to about 100 micrometers. In some embodiments, at least 95% of the particles have a size from about 10 micrometer to about 30 micrometers. In some embodiments, all of the particles have a size from about 10 micrometer to about 250 micrometers.

As persons of ordinary skill in the art are aware, implantable depot compositions having a blend of polymers with different end groups are used the resulting formulation will be able to regulate the duration of delivery. For example, one may use polymers with acid (e.g., carboxylic acid) and ester end groups (e.g., methyl of ethyl ester end groups).

Additionally, by varying the comonomer ratio of the various monomers that form a polymer (e.g., the L/G (lactic acid/glycolic acid) or G/CL (glycolic acid/polycaprolactone) ratio for a given polymer) there will be a resulting depot composition having a regulated burst index and duration of delivery. For example, a depot composition having a polymer with a L/G ratio of 50:50 may have a short duration of delivery ranging from about two days to about one month; a depot composition having a polymer with a L/G ratio of 65:35 may have a duration of delivery of about two months; a depot composition having a polymer with a L/G ratio of 75:25 or L/CL ratio of 75:25 may have a duration of delivery of about three months to about four months; a depot composition having a polymer ratio with a L/G ratio of 85:15 may have a duration of delivery of about five months; a depot composition having a polymer with a L/CL ratio of 25:75 or PLA may have a duration of delivery greater than or equal to six months; a depot composition having a terpolymer of CL/G/L with G greater than 50% and L greater than 10% may have a duration of delivery of about one month and a depot composition having a terpolymer of CL/G/L with G less than 50% and L less than 10% may have a duration months up to six months. In general, increasing the G content relative to the CL content shortens the duration of delivery whereas increasing the CL content relative to the G content lengthens the duration of delivery. Thus, among other things, depot compositions having a blend of polymers having different molecular weights, end groups and comonomer ratios can be used to create a depot formulation having a lower burst index and a regulated duration of delivery.

In various embodiments, the drug depot may comprise a hydrogel made of high molecular weight biocompatible elastomeric polymers of synthetic or natural origin. A desirable property for the hydrogel to have is the ability to respond rapidly to mechanical stresses, particularly shears and loads, in the human body.

Hydrogels obtained from natural sources are particularly appealing since they are more likely to be biodegradable and biocompatible for in vivo applications. Suitable hydrogels include natural hydrogels, such as for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly (acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof. The hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyether-urethane, or a combination thereof.

In various embodiments, rather than directly admixing the therapeutic agent into the drug depot, microspheres may be dispersed within the drug depot, the microspheres loaded with the therapeutic agent. In one embodiment, the microspheres provide for a sustained release of the therapeutic agent. In yet another embodiment, the drug depot, which is biodegradable, prevents the microspheres from releasing the therapeutic agent; the microspheres thus do not release the therapeutic agent until they have been released from the depot. For example, a drug depot may be deployed around a target tissue site (e.g., DRG, synovial joint, etc.). Dispersed within the drug depot are a plurality of microspheres that encapsulate the desired therapeutic agent. Certain of these microspheres degrade once released from the drug depot, thus releasing the therapeutic agent.

Microspheres, much like a fluid, may disperse relatively quickly, depending upon the surrounding tissue type, and hence disperse the therapeutic agent. In some situations, this may be desirable; in others, it may be more desirable to keep the therapeutic agent tightly constrained to a well-defined target site.

Cannula or Needle

It will be appreciated by those with skill in the art that the depot can be administered to the target site using a cannula or needle that can be a part of a drug delivery device e.g., a syringe, a gun drug delivery device, or any medical device suitable for the application of a drug to a targeted organ or anatomic region. The cannula or needle of the drug depot device is designed to cause minimal physical and psychological trauma to the patient.

Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. In various embodiments, the cannula or needle may be inserted using a transforaminal approach in the spinal foramen space, for example, along an inflamed nerve root and the drug depot implanted at this site for treating the condition. Typically, the transforaminal approach involves approaching the intervertebral space through the intervertebral foramina.

Some examples of lengths of the cannula or needle may include, but are not limited to, from about 50 to 150 mm in length, for example, about 65 mm for epidural pediatric use, about 85 mm for a standard adult and about 110 mm for an obese adult patient. The thickness of the cannula or needle will also depend on the site of implantation. In various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge, while the smallest diameter is about 22 gauge. In various embodiments the gauge of the needle or cannula is about 18 to about 22 gauge.

In various embodiments, like the drug depot, the cannula or needle includes dose radiographic markers that indicate location at or near the site beneath the skin, so that the user may accurately position the depot at or near the site using any of the numerous diagnostic imaging procedures. Such diagnostic imaging procedures include, for example, X-ray imaging or fluoroscopy. Examples of such radiographic markers include, but are not limited to, barium, calcium, and/or metal beads or particles.

In various embodiments, the needle or cannula may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the needle or cannula relative to the absence of the material or topography.

The drug depot, pharmaceutical formulation, and/or medical device to administer the drug may be sterilizable. In various embodiments, one or more components of the drug depot, pharmaceutical formulation, and/or medical device to administer the drug are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot is included in a gel.

Other methods may also be used to sterilize the depot, pharmaceutical formulation, and/or one or more components of the device, including, but not limited to, gas sterilization, such as, for example, with ethylene oxide or steam sterilization.

In various embodiments, a kit is provided that may include additional parts along with the drug depot, pharmaceutical formulation, and/or medical device combined together to be used to implant the drug depot (e.g., ribbon-like fibers). The kit may include the drug depot device in a first compartment. The second compartment may include a canister holding the drug depot or pharmaceutical formulation and any other instruments needed for the localized drug delivery. A third compartment may include gloves, drapes, wound dressings and other procedural supplies for maintaining sterility of the implanting process, as well as an instruction booklet. A fourth compartment may include additional cannulas and/or needles. Each tool may be separately packaged in a plastic pouch that is radiation sterilized. A cover of the kit may include illustrations of the implanting procedure and a clear plastic cover may be placed over the compartments to maintain sterility.

In various embodiments, a method for delivering a resolvin into a target tissue site of a patient is provided, the method comprising inserting a cannula at or near a target tissue site and implanting the drug depot containing the resolvin at the target site beneath the skin of the patient. In various embodiments, to administer the drug depot to the desired site, first the cannula or needle can be inserted through the skin and soft tissue down to the target tissue site and the drug depot administered (e.g., injected, implanted, instilled, sprayed, etc.) at or near the target site. In those embodiments where the drug depot is separate from the gel, first the cannula or needle can be inserted through the skin and soft tissue down to the site of injection and one or more base layer(s) of gel can be administered to the target site. Following administration of the one or more base layer(s), the drug depot can be implanted on or in the base layer(s) so that the gel can hold the depot in place or reduce migration. If required a subsequent layer or layers of gel can be applied on the drug depot to surround the depot and further hold it in place. Alternatively, the drug depot may be implanted first and then the gel placed (e.g., brushed, dripped, injected, or painted, etc.) around the drug depot to hold it in place. By using the gel, accurate and precise implantation of a drug depot can be accomplished with minimal physical and psychological trauma to the patient. In various embodiments, the drug depot can be sutured to the target site or alternatively the drug depot can be implanted, without suturing. For example, in various embodiments, the drug depot can be a ribbon shaped depot and placed at the target site, before, during or after surgery.

In various embodiments, when the target tissue site comprises a spinal region, a portion of fluid (e.g., spinal fluid, etc.) can be withdrawn from the target site through the cannula or needle first and then the depot administered (e.g., placed, dripped, injected, or implanted, etc.). The target site will re-hydrate (e.g., replenishment of fluid) and this aqueous environment will cause the drug to be released from the depot.

Treating or treatment of a disease or condition refers to executing a protocol, which may include administering one or more drugs to a patient (human, other normal or otherwise), in an effort to alleviate signs or symptoms of the disease. Alleviation can occur prior to signs or symptoms of the disease or condition appearing, as well as after their appearance. Thus, "treating" or "treatment" may include "preventing" or "prevention" of disease or undesirable condition. In addition, "treating" or "treatment" does not require complete alleviation of signs or symptoms, does not require a cure, and specifically includes protocols that have only a marginal effect on the patient. "Reducing pain" includes a decrease in pain and does not require complete alleviation of pain signs or symptoms, and does not require a cure. In various embodiments, reducing pain includes even a marginal decrease in pain. By way of example, the administration of one or more effective dosages of the resolvin may be used to prevent, treat or relieve the symptoms of post-operative pain and/or inflammation incidental to surgery.

"Localized" delivery includes, delivery where one or more drugs are deposited within, at or near a tissue. For example, localized delivery includes delivery to a nerve root of the nervous system or a region of the brain, or in close proximity (within about 10 cm, or preferably within about 5 cm, for example) thereto. "Targeted delivery system" provides delivery of one or more drugs depots (e.g., gels or depot dispersed in the gel, etc.) having a quantity of therapeutic agent that can be deposited at or near the target tissue site as needed for treatment of pain and/or inflammation incidental to surgery.

The term "patient" refers to organisms from the taxonomy class "mammalian," including but not limited to humans, other primates such as chimpanzees, apes orangutans and monkeys, rats, mice, cats, dogs, cows, horses, etc.

In various embodiments, a strategy of triangulation may be effective when administering multiple drug depot formulations. Thus, a plurality (at least two, at least three, at least four, at least five, at least six, at least seven, etc.) drug depots comprising the pharmaceutical formulations may be placed around the target tissue site (also known as the pain generator or pain generation site) such that the target tissue site falls within a region that is either between the formulations when there are two, or within an area whose perimeter is defined by a set of plurality of formulations.

In various embodiments, the drug depot comprising the resolvin can be made by combining a biocompatible polymer (as discussed above) and a therapeutically effective amount of a resolvin or pharmaceutically acceptable salt thereof and forming the implantable drug depot from the combination.

Various techniques are available for forming at least a portion of a drug depot from the biocompatible polymer(s), therapeutic agent(s), and optional materials, including solution processing techniques and/or thermoplastic processing techniques. Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise, one or more of the following: a resolvin and other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: a resolvin, optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, a resolvin may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the therapeutic agent, if it were present. This precompounded material is then mixed with the therapeutic agent under conditions of lower temperature and mechanical shear, and the resulting mixture is shaped into the resolvin containing drug depot. Conversely, in another embodiment, the biocompatible polymer can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot is formed comprising PLGA or PLA polymer, a radio-opacifying agent (e.g., bismuth subcarbonate), and a therapeutic agent prone to degradation by heat and/or mechanical shear (e.g., a resolvin), in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min). It is noted that this processing temperature is well below the melting points of different resolvins, because processing at or above these temperatures will result in substantial therapeutic agent degradation. It is further noted that in certain embodiments, the processing temperature will be below the melting point of all bioactive compounds within the composition, including the therapeutic agent. After compounding, the resulting depot is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or a viscosity enhancing agent), whereupon the therapeutic agent is imbibed on or in the drug depot. As above, the resulting solid material can then be granulated for further processing, if desired.

Typically, an extrusion processes may be used to form the drug depot comprising a biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., ribbon, pellet, strip, etc.) is cooled. Examples of cooling processes include air cooling and/or immersion in a cooling bath. In some embodiments, a water bath is used to cool the extruded depot. However, where a water-soluble therapeutic agent such as a resolvin is used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this release profile is not desired.

In various embodiments, the drug depot can be prepared by mixing or spraying the drug with the polymer and then molding the depot to the desired shape. In various embodiments, the resolvin is used and mixed or sprayed with the PLGA or PEG550 polymer, and the resulting depot may be formed by extrusion and dried.

Materials other than pharmaceutically acceptable polymers may also be used to prepare a pharmaceutical composition for the sustained release of the resolvin. In one embodiment of the invention, the composition for sustained release comprises a vesicular phospholipid gel. Vesicular phospholipid gels are disclosed in published patent application US2010/0239654 "Vesicular Phospholipid Gels Comprising Proteinaceous Substances" incorporate herein in its entirety.

In other embodiments of the invention, beta tricalcium phosphate or hydroxyapatite could be utilized to deliver the drug. Further, while a controlled release depot is a preferred embodiment, the drug could be administered topically. Suitable formulations for this mode of administration would include cream topicals. Example of cream topicals include, but are not limited to, hydrogels, such as polyethylene oxide and organogels, such as vegetable oil.

The desired mode of administration and the particular formulation for drug delivery depend, in part, on the desired target location of the therapy. Utilizing the teachings of the present specification, one skilled in the art could design the appropriate mode of administration.

For example, for intra-discal injection, a carrier may be passive due to the low fluid turn-over and avascular compartment of the intravertebral disc. Here a passive carrier would not necessarily require a controlled release profile. Intradiscally, the compression of the disc during activity could effectively "squeeze out" the resolvins from the carrier. Once released in this environment, the drug would have a longer residence time due to the local fluid clearance from the disc. Conversely, for intra-articular injection, fluid is cleared regularly and rapidly, so a local delivery over time would be desirable to maintain clinically relevant levels of the therapeutic. In one embodiment of the invention, microspheres are utilized to provide the appropriate local delivery of the drug.

As mentioned, additional therapeutic agents may be included in the formulation with the resolvin therapy. Suitable additional agents include, but are not limited to antibiotics, NSAIDS and hormones, such as progesterone. Further examples of suitable additional therapeutic agents include, but are not limited to, analgesics, anesthetics, antimicrobial agents, antibacterial agents, antiviral agents, antifungal agents, antibiotics, antiseptic agents, antioxidants, immunstimulating agents and combinations thereof. The resolvin and other agents may be administered sequentially or concomitantly/simultaneously.

Additional therapeutic agents that may be used in the resolvin therapy include those that are direct- and local-acting modulators of pro-inflammatory cytokines such as TNF-α and IL-1 including, but not limited to, soluble tumor necrosis factor α receptors, any pegylated soluble tumor necrosis factor α receptor, monoclonal or polyclonal antibodies or antibody fragments or combinations thereof.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments and other embodiments not specifically described herein, will be apparent to those of skill in the art upon reviewing the above description.

While the invention has been shown and described with respect to particular embodiments, it is not thus limited. Numerous modifications, changes and enhancements will now be apparent to the reader.

What is claimed is:

1. A method for treating inflammation comprising locally administering one or more drug depots comprising a therapeutically effective amount of at least one resolvin to at least one of a muscle, ligament, tendon and cartilage of a patient in need of treatment, the drug depot comprising a polymer comprising dextran.

2. The method of claim 1, wherein the drug depot comprises a lipid.

3. The method of claim 1, wherein the inflammation is result of periodontal disease.

4. The method of claim 1, further comprising an additional therapeutic agent.

5. The method of claim 4 wherein the additional therapeutic agent is an NSAID.

6. A method of treating inflammation comprising locally administering one or more drug depots comprising a biodegradable polymer comprising dextran, the drug depot comprising a therapeutically effective amount of at least one resolvin to at least one of a muscle, ligament, tendon and cartilage of a patient in need of treatment.

7. The method of claim 6 wherein the drug depot comprises microparticles, microspheres, microcapsules and/or microfibers suspended in a gel.

8. The method of claim 6 wherein the inflammation is chronic inflammation.

9. The method of claim 6 wherein the drug depot comprises an additional therapeutic agent.

10. The method of claim 8 wherein the chronic inflammation is a result of periodontal disease.

11. The method of claim 6 wherein the drug depot comprises a controlled release formulation.

12. The method of claim 6 wherein the drug depot provides an initial burst of resolvin therapy.

13. The method of claim 6, wherein the resolvin is administered by local injection or infusion.

14. A method for treating inflammation comprising locally administering one or more drug depots comprising a therapeutically effective amount of at least one resolvin to at least one of a muscle, ligament, tendon and cartilage of a patient in need of treatment, the drug depot comprising a polymer comprising dextran, the drug depot further comprising an NSAID.

15. The method of claim 14, wherein the drug depot provides a controlled release of the resolvin.

16. The method of claim 14 wherein the drug depot comprises microparticles, microspheres, microcapsules and/or microfibers suspended in a gel.

* * * * *